United States Patent [19]
Zhao et al.

[11] Patent Number: 5,287,725
[45] Date of Patent: Feb. 22, 1994

[54] SURFACE VOLATILE MATERIAL DETECTOR

[75] Inventors: Jun Zhao, Milpitas; Laszlo Szalai, Campbell; Boris Fishkin; Terry Francis, both of San Jose, all of Calif.

[73] Assignee: Applied Materials, Inc., Santa Clara, Calif.

[21] Appl. No.: 82,142

[22] Filed: Jun. 23, 1993

Related U.S. Application Data

[63] Continuation of Ser. No. 799,822, Nov. 26, 1991, abandoned.

[51] Int. Cl.$^5$ .............................................. G01N 1/22
[52] U.S. Cl. .................................................... 73/23.2
[58] Field of Search .......................... 73/23.2, 19.01

[56] References Cited

U.S. PATENT DOCUMENTS

| | | | |
|---|---|---|---|
| 4,660,976 | 4/1987 | Falk | 356/312 |
| 4,965,209 | 10/1990 | Smith | 436/32 |

FOREIGN PATENT DOCUMENTS

| | | | |
|---|---|---|---|
| 0395194A2 | 10/1990 | European Pat. Off. | |
| 3203912A1 | 8/1983 | Fed. Rep. of Germany. | |
| 2627285 | 8/1989 | France | 73/23.2 |
| 201551 | 8/1988 | Japan | 73/23.2 |
| 1-274045 | 11/1989 | Japan. | |
| 254336 | 10/1990 | Japan | 73/19.01 |
| 41341 | 2/1991 | Japan | 73/23.2 |
| 2114736B | 1/1986 | United Kingdom. | |

*Primary Examiner*—Hezron E. Williams
*Assistant Examiner*—Joseph W. Roskos
*Attorney, Agent, or Firm*—Raymond R. Moser

[57] ABSTRACT

Surface Volatile Material Detector including a vacuum chamber that is adapted to hold a silicon wafer for testing. The surface of the wafer is exposed to a heat source which evaporates the volatile contaminants on the surface of the wafer. A gas composition analyzer samples the atmosphere within the chamber to detect the evaporated contaminants. The device is designed such that the wafer is thermally insulated from the chamber, whereby the wafer is heated while the chamber walls remain cool, and any contaminants which might exist on the walls of the chamber are not evaporated. In the preferred embodiment, the wafer is heated by infrared light illumination.

20 Claims, 5 Drawing Sheets

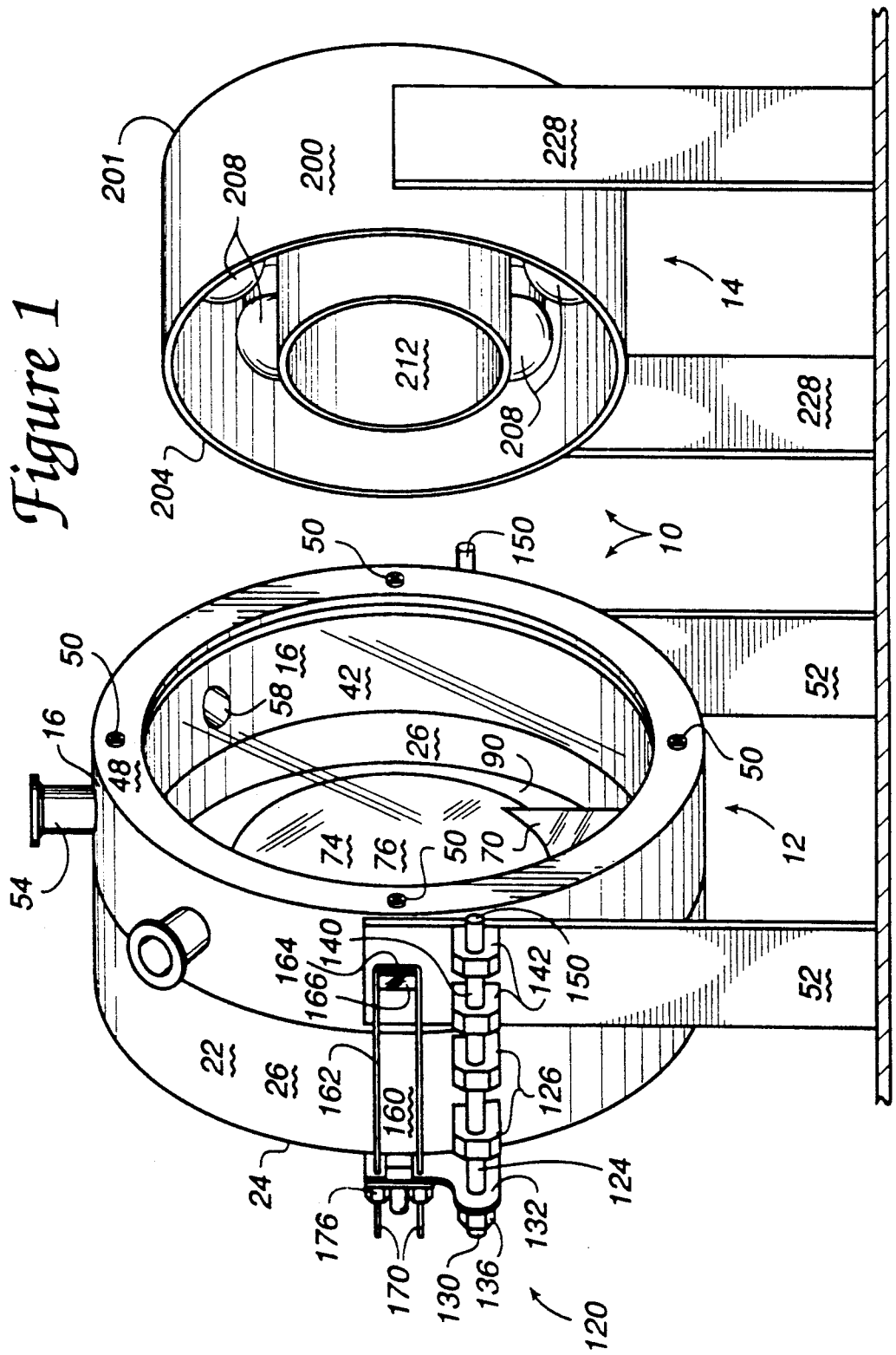

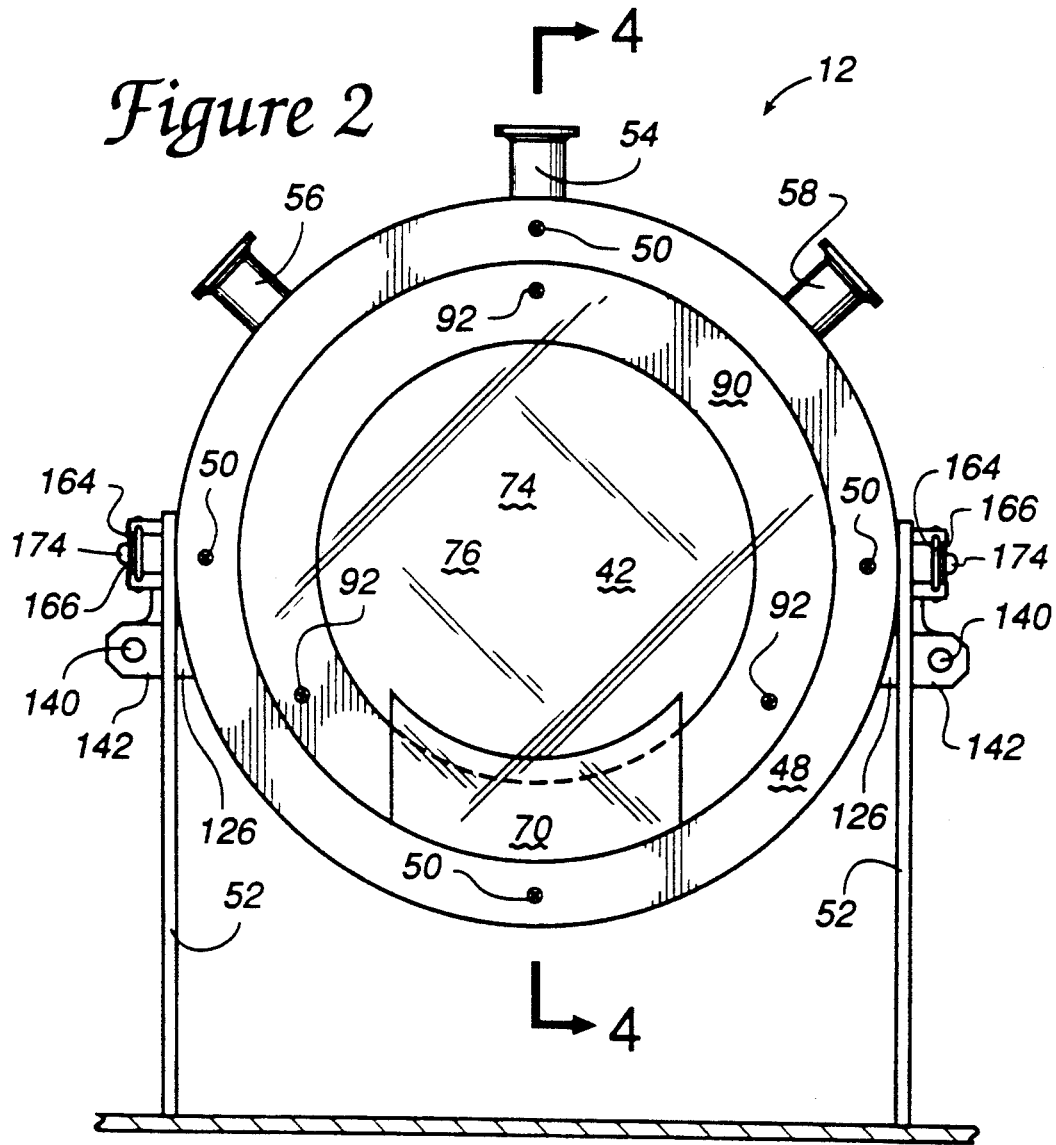

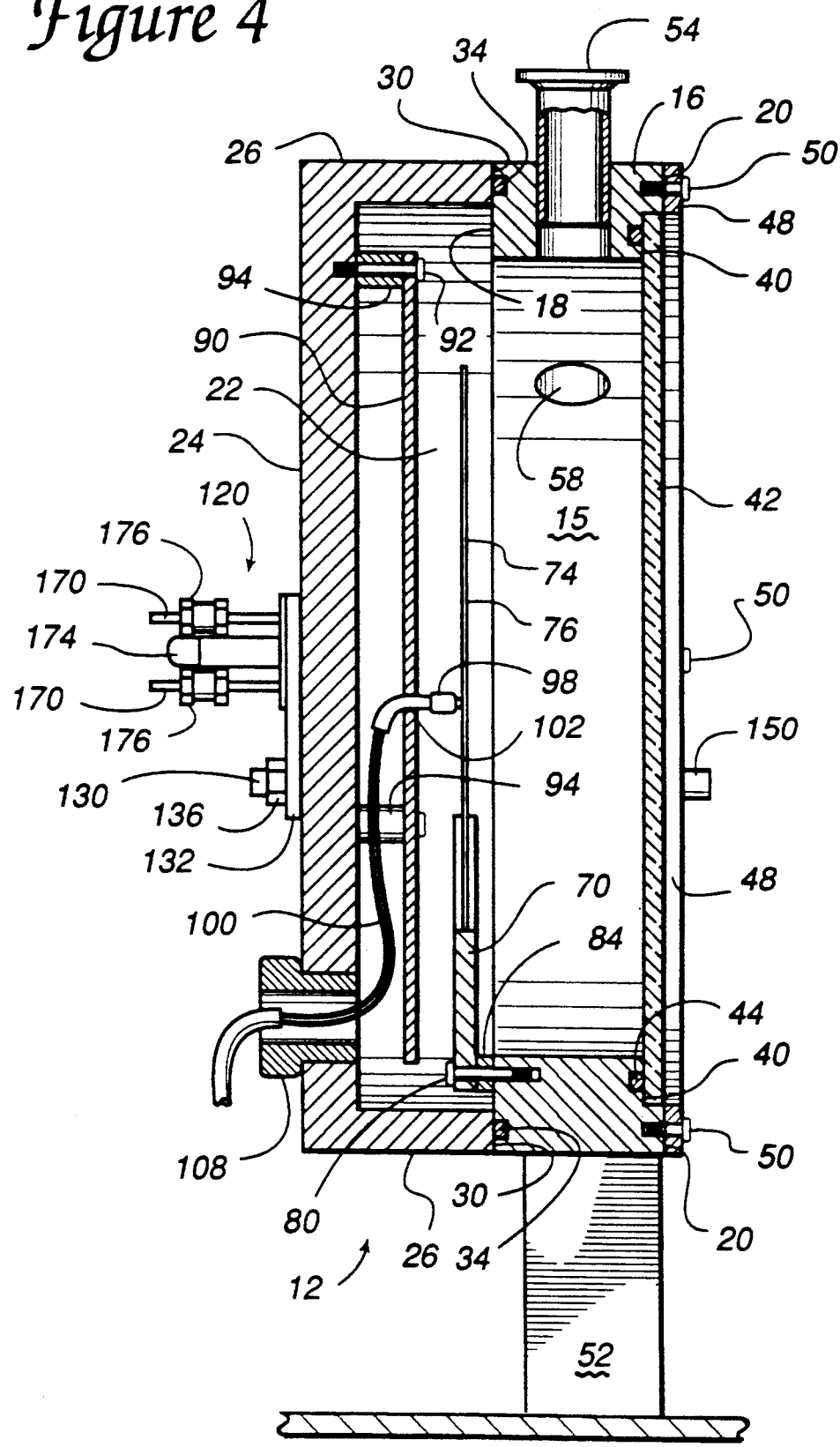

SURFACE VOLATILE MATERIAL DETECTOR

This is a continuation of U.S. application Ser. No. 07/799,822, filed Nov. 26, 1991. now abandoned.

BACKGGROUND OF THE INVENTION

1. Field of the Invention

The present invention relates generally to devices for detecting particulate contamination upon the surface of silicon wafers, and more particularly to devices which heat the surface of the wafer to evaporate volatile contaminants therefrom for detection.

b 2. Brief Description of the Prior Art

Foreign materials which contaminate the surface of silicon wafers are currently detected and analyzed utilizing a scanning electron microscope (SEM), and/or an energy dispersive spectrometer (EDS). However, volatile contaminants are not easily detected by SEM devices because such contaminants evaporate and become invisible under the electron beam. Contaminants which include light elements such as hydrogen and boron are not easily detected by EDS devices due to their small mass. There is, therefore, a need for a device which can easily and rapidly detect volatile contaminants upon the surface of wafers.

SUMMARY OF THE INVENTION

The surface volatile material detector includes a vacuum chamber that is adapted to hold a silicon wafer for testing. The surface of the wafer is exposed to a heat source which evaporates the volatile contaminants on the surface of the wafer. A gas composition analyzer samples the atmosphere within the chamber to detect the evaporated contaminants. The device is designed such that the wafer is thermally insulated from the chamber, whereby the wafer is heated while the chamber walls remain cool, and any contaminants which might exist on the walls of the chamber are not evaporated. In the preferred embodiment, the wafer is heated by infrared light illumination.

It is an advantage of the present invention that it provides a detector that is sensitive to surface volatile material contaminants, whether particulates or films.

It is another advantage of the present invention that it provides a device wherein the wafer can be rapidly heated, whereby a more intense contaminant signal is produced.

It is a further advantage of the present invention that it provides a device wherein the wafer is heated by infrared radiation and wherein the device is designed with reflective walls, such that the infrared radiation rapidly heats the wafer.

It is yet another advantage of the present invention that it provides a device wherein the heated wafer is thermally insulated from the walls of the chamber, whereby any contaminants disposed upon the walls of the chamber are not heated or evaporated, such that the evaporated contaminants within the chamber originate only from the heated wafer.

It is yet a further advantage of the present invention that it provides a device which rapidly and easily detects volatile surface contaminants, such as water moisture, chlorine, bromine and other outgassing contaminants.

These and other features and advantages of the present invention will become apparent to one skilled in the art from the following description of the preferred embodiment which makes reference to the several figures of the drawing.

IN THE DRAWING

FIG. 1 is a perspective view of the present invention;

FIG. 2 is a front elevational view of the wafer chamber of the present invention;

FIG. 4 is a side cross-sectional view of the wafer chamber, taken along lines 4—4 of FIG. 2;

DETAILED DESCRIPTION OF THE PREFERRED EMBODIMENT

Figure 3:
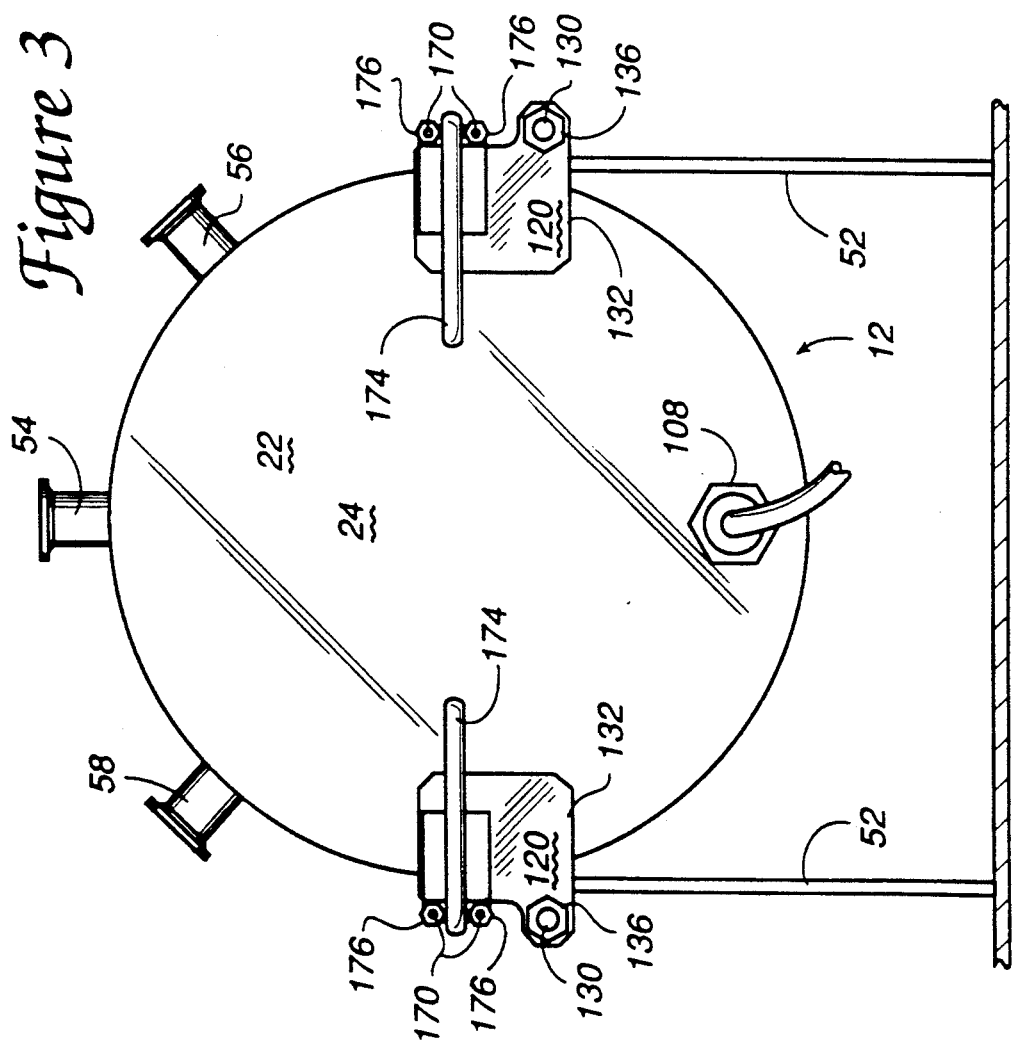
FIG. 3 is a rear elevational view of the wafer chamber.

As depicted in FIG. 1, the surface volatile material detector of the present invention includes a wafer holding chamber 12 and a wafer heater 14. It is to be understood that while both the Wafer chamber 12 and wafer heater 14 are shown in perspective view in FIG. 1, they are shown from a different point of view for ease of description. In operation, the two devices 12 and 14 are positioned to face each other, such that infrared light from the wafer heater 14 is directed into the wafer chamber 12. The detailed components and features of the wafer chamber 12 are best understood with the aid of FIGS. 2, 3 and 4.

The wafer chamber 12 includes a generally cylindrical forward chamber portion 15 including a chamber side wall 16 having a rearward face 18 and a frontward face 20. The wafer chamber 12 has a back portion 22 including a generally disc-like back wall 24 that is formed with an annular side wall 26 which projects forwardly from the outer edge of the back wall 24. The projecting side wall 26 is formed with a forward face 30 which is disposed to mate with the rearward face 18 of the chamber side wall 16. As will be more fully understood from the disclosure hereinbelow, the faces 18 and 30 are formed to create a vacuum seal, and an 0-ring seal 34 is disposed within the face 18 to mate with face 30 and facilitate such a vacuum seal. An annular shoulder 40 is formed in the front face 20 of the side wall 16 to permit the installation of a circular quartz glass window 42 therein. An 0-ring seal 44 is disposed within the shoulder 40 to facilitate the formation of a vacuum seal for the chamber 12. A ring-shaped sealing plate 48 is engaged to the front face 20, such as by plate screws 50 to hold the quartz glass window 42 in position within the shoulder 40. The forward chamber portion 15 is supported by a chamber mounting frame represented by two leg members 52, and the back chamber portion 22 is engaged to the forward portion 15 utilizing a chamber engagement mechanism that is described hereinbelow.

Three ports are formed through the side wall 16 into the chamber 12. A first port 54 is utilized as a vacuum port to create a low pressure environment within the chamber 12. A second port 56 is utilized as a sampling port to permit the sampling of the atmosphere within the chamber utilizing a gas analyzer. The third port 58 is utilized as an inlet port to permit the inletting of a gas, such as dry nitrogen, into the chamber 12.

A wafer holding mount 70 is disposed within the chamber 12 to hold a generally circular silicon wafer 74 within the chamber, such that the flat surface 76 of the wafer 74 faces the window 42. In the preferred embodiment, the wafer mount 70 is engaged to the lower portion of the rearward face 18 of the side wall 16, such as through the utilization of at least one mounting screw 80. In the preferred embodiment, an insulating washer 84 is disposed between the wafer mount 70 and the rearward face 18, to inhibit heat transfer between the wafer mount and the walls 16 of the chamber 12.

As is best seen in FIG. 4, a heat reflecting disc 90 is disposed behind the wafer 74. The disc 90 is engaged to the back wall 24 utilizing screws 92. In the preferred embodiment, an insulating washer 94 is disposed upon the screws 92 between the heat reflecting disc 90 and the back wall 24 to inhibit heat transfer between the disc 90 and the back wall 24.

A wafer temperature sensor 98 is provided within the chamber 12 to provide electrical signals indicative of the temperature of the wafer through electrical lines 100. In the preferred embodiment, the temperature sensor 98 is engaged through a small orifice 102 formed in the disc 90, such that the heat sensitive element of the sensor 98 makes physical contact with the wafer 74. The temperature sensor wires 100 exit the vacuum chamber 12 through a vacuum seal 108 which penetrates the back wall 24.

The chamber 12 is preferably designed with a forward chamber portion 15 and a back portion 22 that separate to form a gap at the vacuum seal ring 34, such that wafers 74 may be inserted into and removed from the wafer mount 70 through the gap. To facilitate the opening and closing of the chamber, a chamber engagement mechanism is provided, as is next discussed.

The chamber engagement mechanism includes two locking devices 120, one of which is disposed on each side of the chamber 12. Both devices 120 are substantially identical, whereby only one of said locking devices 120 will be described herein. The chamber locking device 120 includes a guide bar 124 which is fixedly engaged within two bar clamping members 126 that project from the outer surface of the wall sections 26 of the back wall 24. The rearward end 130 of the guide bar 124 passes through a hole formed in a mounting bracket 132 that is engaged to the rearward surface of the back wall 24, and a nut 136 is threadably engaged to the end 130 of the guide bar 124. It is therefore to be understood that the back portion 22 of the chamber 12 is fixedly engaged to the guide bar 124. The frontward portion 140 of the guide bar 124 is slidably engaged in two guide bar mounting brackets 142 that are fixedly engaged to the wafer chamber mounting frame 52. The forwardmost end 150 of the guide bar 124 projects forwardly of the mounting brackets 142, such that when the back portion 22 of the wafer chamber 12 is displaced rearwardly, the guide bar 124 will maintain a slidable engagement within the mounting brackets 142. It is therefore to be understood that the back portion 22 of the wafer chamber 12 is slidably engaged to the forward portion 15 of the chamber 12 through the utilization of the two guide bars 124.

Each locking device 120 further includes a chamber securement mechanism 160 which serves to releasably hold the forward portion 15 and back portion 22 of the chamber together. In the preferred embodiment, the securement mechanism 160 includes a U-shaped rod-like clamp 162 that is disposed such that the base portion 164 of the U-shaped clamp 162 engages a chamber securement projection 166 which projects from the chamber frame member 52. The two projecting ends 170 of the U-shaped clamp 162 are fixedly engaged to a lever mechanism 174 that is pivotly engaged to the mounting bracket 132. It is therefore to be understood that pivotal motion of the lever 174 will cause the base portion 164 of the clamp 162 to move in a forward or rearward direction. Adjustment nuts 176 are threadably engaged to the ends 170 to provide for appropriate adjustment of the securement mechanism 160. It is to be understood that such securement mechanisms 160 are well known in the prior art, such as those found on the proverbial steamer trunk, tool box, lunch pail, and many other applications. The present invention is not to be limited to the type of locking mechanism 120 discussed hereinabove, and it is within the contemplation of the inventors that many different types of chamber access mechanisms could be utilized to permit the insertion and removal of wafers 74 from the chamber 12. The present invention is deemed to include all such mechanisms as would provide for insertion and removal of wafers from the chamber 12.

Figure 5:
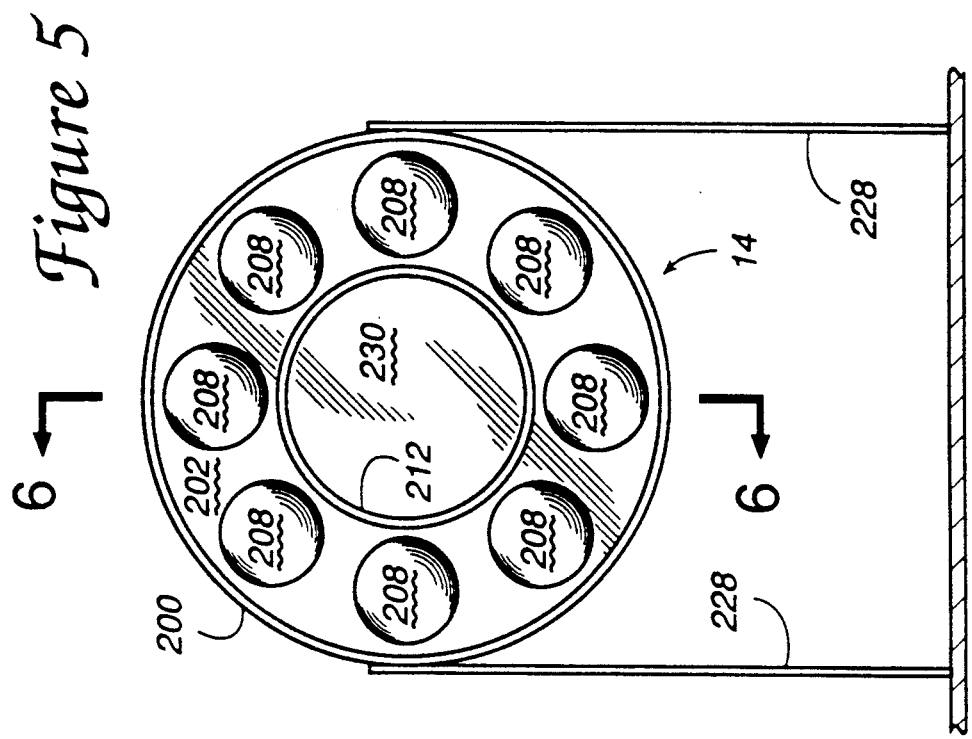
FIG. 5 is a front elevational view of the wafer heater of the present invention.
Figure 6:
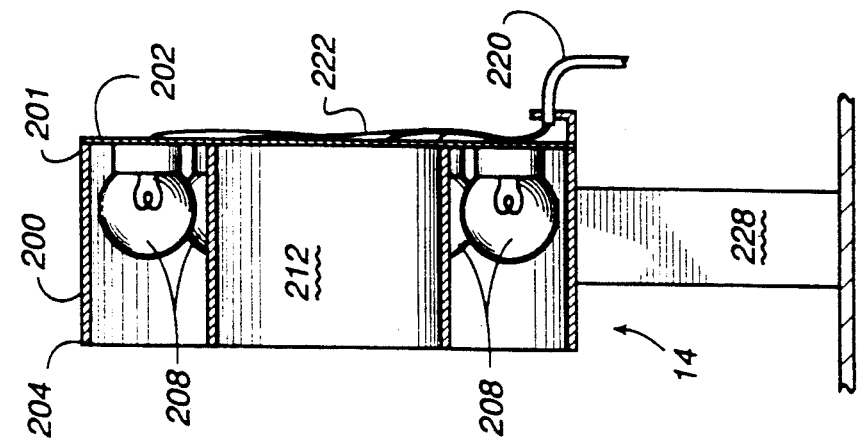
FIG. 6 is a side cross-sectional view of the wafer heater, taken along lines 6—6 of FIG. 5.

As has been mentioned hereinabove, in the preferred embodiment the wafer 74 is preferably heated utilizing infrared radiation. The preferred invention utilizes a wafer heater 14 which projects a collimated infrared light beam that is directed through the quartz glass window 42 upon the front surface 76 of the wafer 74. The wafer heater 14 is best described with the aid of FIGS. 1, 5 and 6, wherein FIG. 1 is a perspective view, FIG. 5 is a front elevational view and FIG. 6 is a side cross-sectional view taken along lines 6—6 of FIG. 5. The wafer heater 14 includes a generally cylindrical outer wall 200 having a rearward end 201 that is closed by a back plate 202 and an open light-emitting front end 204. A plurality of infrared light emitting bulbs 208 are engaged symmetrically around the back plate 202 to emit infrared light from the front end 204 of the heater 14. A cylindrical inner wall 212 is centrally disposed relative to the outer cylindrical wall 200 to provide a light directing and collimating function to the heater 14. In the preferred embodiment, an infrared light reflective coating is placed upon all inner surfaces of the heater 14, including the inner surface of the back plate 202, the inner and outer surfaces of the inner cylindrical wall 212 and the inner surface of the outer cylindrical wall 200. Electrical power to the infrared light bulbs 208 is provided through an electrical cable 220 and suitable electrical wiring 222 to each bulb 208. The heater 14 is supported by a frame represented by two leg members 228.

It is therefore to be understood that infrared light which emanates from the bulbs 208 is projected directly and by the reflective coatings within the heater 14 towards the wafer chamber 12, through the front glass plate 42 and onto the front surface 76 of the wafer 74. A significant portion of the infrared radiation will pass through the silicon wafer 74 and be reflected back through the wafer by the reflecting back plate 90 behind the wafer 74. The reflected light again heats the wafer upon passing therethrough, and a portion of the reflected light will again pass through the wafer 74. The reflected light then illuminates the reflective surfaces of the wafer heater such as the central portion 230 of the backing plate 202, and is reflected back once again to the wafer for further heating thereof. The multiple passes of the infrared light through the wafer, caused by the reflective surfaces, serves to more rapidly heat the wafer, whereby a rapid vaporization of contaminants is achieved and a more intense contaminant signal results.

Figure 7:
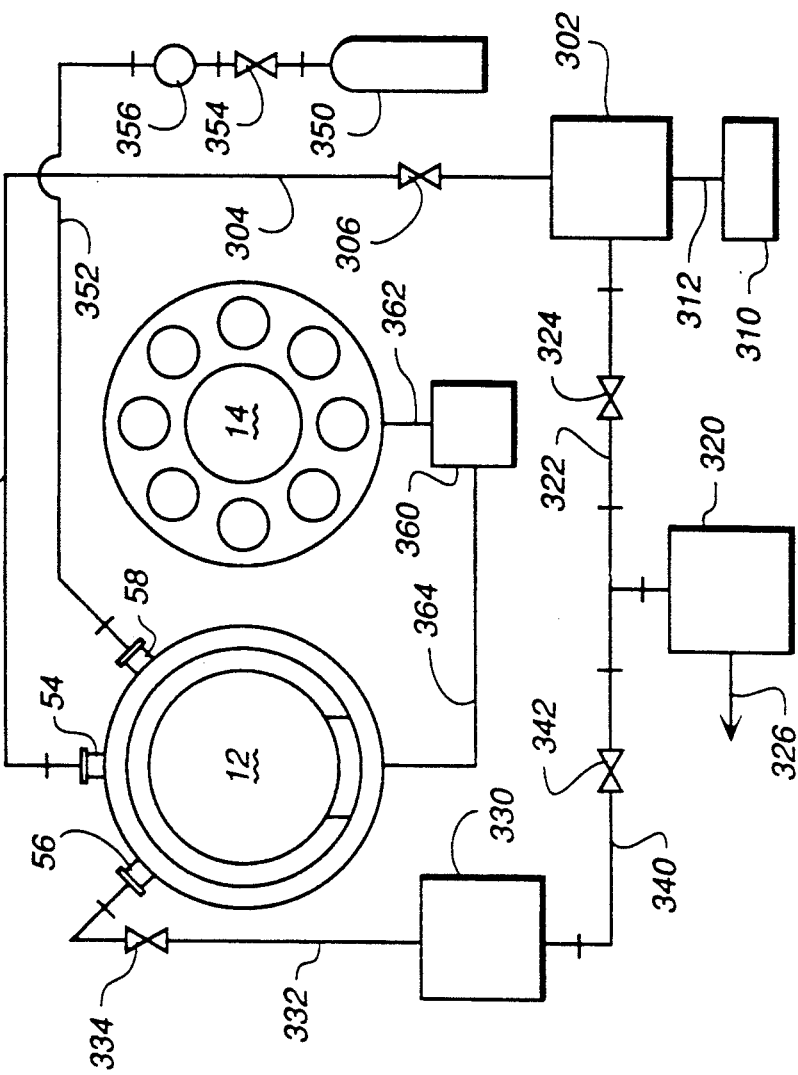
FIG. 7 is a schematic diagram of the method and apparatus of the present invention as utilized to detect surface volatile material contaminants upon a wafer.

FIG. 7 provides a schematic diagram of the apparatus and method of the present invention. As depicted therein, the vacuum port 54 of the wafer chamber 12 is connected to a vacuum pump 302 through a suitable vacuum line 304 and valve 306. In the preferred embodiment, the vacuum pump 302 is controlled by an electronic controller 310 through an appropriate electrical connection 312. In the preferred embodiment, the vacuum pump 302 is a magnetic suspended pump which is not oil lubricated, whereby contamination of the wafer chamber is avoided. The preferred vacuum pump 302 is a turbo pump manufactured by Osaka Vacuum Limited, Model Number TG363M. As is well known to those skilled in the art, the proper operation of turbo pump 302 requires connection to a further vacuum pump 320 through an appropriate vacuum line 322 and valve 324. In the preferred embodiment, the vacuum pump 320 is an Edwards Company dry pump, Model DP40 which has a vacuum pump exhaust outlet 326. It is therefore to be realized that the operation of the vacuum pumps 320 and 302 serves to provide a low pressure environment within the chamber 12.

The chamber samplinq port 56 is connected to a gas composition analyzer 330 through an appropriate gas connection line 332 and valve 334. In the preferred embodiment, the gas composition analyzer 330 is preferably a residual gas analyzer (RGA) such as the UTI Precision Mass Analyzer Model Number 100C. The line 332 is preferably made as short as possible to facilitate the rapid, accurate detection of vaporized contaminants which must travel through the line 332 to the RGA 330. To facilitate the proper operation of the RGA, it is connected through a suitable gas line 340 and valve 342 to the vacuum pump 320, as is well known to those skilled in the art.

The inlet port 58 of the chamber 12 is connected to a suitable source of a dry pure gas for establishing an appropriate atmosphere within the chamber 12. In the preferred embodiment, the inlet port 58 is connected to a cylinder 350 containing dry nitrogen gas utilizing a suitable gas line 352, valve 354 and pressure regulator 356.

The heater 14 is controlled utilizing an electronic controller 360 through an electrical connection line 362. The temperature sensor 98 disposed within the chamber 12 is electrically connected through electrical line 364 to the heater controller 360 to provide control feedback signals for the heating of the wafer 74 to the desired temperature range for vaporization of the surface contaminants disposed thereon.

The measurement procedure utilizing the present invention includes the following steps. A wafer is mounted on the wafer holder in the open chamber. The chamber is closed and locked and then flushed with high purity dry nitrogen gas from source 350 through the inlet port 58. The chamber is then pumped down through vacuum port 54 utilizing the dry pump 320 and turbo pump 302 to a low pressure which is most suitable for the gas analyzer 330. The wafer 74 is then heated utilizing the heater 14 with feedback through the temperature sensor 98 to an appropriate temperature for the vaporization of surface contaminants upon the face 76 of the wafer 74. A typically suitable temperature is approximately 400 degrees centigrade. The vaporized contaminants are then analyzed utilizing the gas composition analyzer 330. During heating and analysis, dry nitrogen is bled into the chamber 12 through line 352 to carry the vaporized contaminants to the analyzer 330 through the line 332. The bleeding rate is balanced with the analyzer sampling rate to keep a constant chamber pressure.

It is a feature of the present invention that the wafer is rapidly heated using collimated infrared illumination while the chamber walls are kept cool. This feature is achieved utilizing collimated infrared light, the back reflector disc 90, rapid wafer heating and the insulation of the wafer holder and back reflector disc 90 from the chamber walls. The cool chamber walls prevent any contaminants disposed thereon from being vaporized and thereby producing false results.

The feature of rapid wafer heating is important in that it produces a more intense contaminant signal. In the present invention, the wafer can be heated to approximately 400 degrees centigrade within two minutes. This rapid heating is achieved by the method of multiple passages of the infrared beam through the wafer that is achieved by the utilization of the reflective disc 90 and the reflective surfaces within the heater 14. In the preferred embodiment, the chamber gas that is utilized may be nitrogen, helium or argon having a purity of less than one part per billion of contaminants.

The present invention is very sensitive to surface volatile materials. It is estimated that a one micron particle, when completely evaporated can produce about one part per million impurity level within the chamber at 1.0 mTorr background pressure. This one part per million level can be easily detected by a high sensitivity (RGA) with a detection limit of one part per billion. The present invention is even more sensitive to adsorbed films on the wafer as such films generally contain much more mass than a single one micron particle.

While the present invention has been particularly shown and described with reference to certain preferred embodiments, it will be understood by those skilled in the art that various alterations and modifications in form and in detail may be made therein. Accordingly, it is intended that the following claims cover all such alterations and modifications as may fall within the true spirit and scope of the invention.

What is claimed is:

1. A surface volatile material detector, comprising:
    a chamber, said chamber having walls enclosing and defining a space within said chamber;
    a wafer holding means, said water holding means being disposed within said chamber and functioning to hold a wafer therewithin;
    a wafer heating means, said wafer heating means functioning to provide heat energy to said wafer held within said wafer holding means, whereby a volatile contaminant that is disposed upon a surface of said wafer will be vaporized by exposure to said heat energy;
    a wafer temperature sensing means, said wafer temperature sensing means being disposed within said chamber and functioning to detect the temperature of a wafer disposed therein;
    a gas analyzer means, said gas analyzer means being engaged to said chamber and functioning to detect said vaporized volatile contaminants.

2. A surface volatile material detector as described in claim 1, further including a vacuum means, said vacuum means being engaged to said chamber and functioning to provide a reduced atmospheric pressure within said chamber.

3. A surface volatile material detector as described in claim 2 wherein said chamber is filled with a dry, relatively inert gas, and said gas analyzer means comprises a low pressure residual gas analyzer.

4. A surface volatile material detector as described in claim 1 wherein said chamber further includes a wafer insertion and removal means, said wafer insertion and removal means functioning to permit a wafer to be inserted into said chamber for mounting within said wafer holding means, and permitting a wafer to be removed from said wafer holding means and said chamber.

5. A surface volatile material detector as described in claim 4 wherein said wafer insertion and removal means includes a sealable gap being formed in said walls of said chamber, said gap being selectively openable to insert or remove a wafer from said chamber, and said gap being closeable such that said chamber walls are sealed.

6. A surface volatile material detector as described in claim 5 wherein said wafer insertion and removal means includes a chamber locking means, said chamber locking means functioning to releasably seal said gap in a closed orientation.

7. A surface volatile material detector as described in claim 1 wherein said wafer heating means is disposed externally of said chamber walls, and wherein a segment of said chamber walls is composed of a heat energy transmissive substance, whereby said heat energy may be transmitted through said heat energy transmissive substance to heat a wafer disposed within said chamber.

8. A surface volatile material detector as described in claim 7 wherein said heat energy transmissive substance comprises a quartz glass window, said window being disposed within said chamber walls and forming a part thereof, and wherein said wafer heating means comprises an infrared light energy source which is disposed to project infrared energy through said window to illuminate and heat said wafer within said chamber.

9. A surface volatile material detector as described in claim 1 wherein said wafer temperature sensing means is adapted to output a wafer temperature electrical signal indicative of the temperature thereof;

said wafer heating means further including a wafer heater controlling means, said wafer heater controlling means functioning to control the heat energy output of said wafer heating means; and wherein said wafer temperature electrical signal is provided to said wafer heating controlling means to provide electrical feedback to control said wafer heater means.

10. A surface volatile material detector, comprising:
a chamber, said chamber having walls enclosing and defining a space within said chamber;
a wafer holding means, said wafer holding means being disposed within said chamber and functioning to hold a wafer therewithin;
a wafer heating means, said wafer heating means functioning to provide heat energy to said wafer held within said wafer holding means, whereby a volatile contaminant that is disposed upon a surface of said wafer will be vaporized by exposure to said heat energy; said wafer heating means being disposed externally of said chamber, and wherein a segment of said chamber walls is composed of a heat energy transmissive substance, whereby said heat energy may be transmitted through said heat energy transmissive substance to heat a wafer disposed within said chamber; said heat energy transmissive substance comprising a quartz glass window, said window being disposed within said chamber walls and forming a part thereof, and wherein said wafer heating means comprises an infrared light energy source which is disposed to project infrared energy through said window to illuminate and heat said wafer within said chamber;
a heat energy reflector means, said heat energy reflector means being disposed within said chamber and functioning to reflect heat energy which passes through said wafer back towards said wafer;
a gas analyzer means, said gas analyzer means being engaged to said chamber and functioning to detect said vaporized volatile contaminants.

11. A surface volatile material detector as described in claim 10 wherein said heat energy reflector means includes a heat reflecting plate, said heat reflecting plate being disposed on a side of said wafer away from said wafer heating means.

12. A surface volatile material detector, comprising:
a chamber, said chamber having walls enclosing and defining a space within said chamber;
a vacuum means, said vacuum means being engaged to said chamber and functioning to provide a reduced atmospheric pressure within said chamber;
a wafer holding means, said wafer holding means being disposed within said chamber and functioning to hold a wafer therewithin;
a wafer heating means, said wafer heating means being disposed externally of said chamber walls and functioning to provide heat energy to said wafer;
a segment of said chamber walls being composed of a heat energy transmissive substance, whereby said heat energy may be transmitted through said heat energy transmissive substance to heat said wafer disposed within said chamber, whereupon a volatile contaminant that is disposed upon a surface of said wafer will be vaporized by exposure to said heat energy;
a wafer temperature sensing means, said wafer temperature sensing means being disposed within said chamber and functioning to detect the temperature of said wafer disposed therein: said wafer temperature sensing means being adapted to output a wafer temperature electrical signal indicative of the temperature thereof;
said wafer heating means further including a wafer heater controlling means, said wafer heater controlling means functioning to control the heat energy output of said wafer heating means; said wafer temperature electrical signal being provided to said wafer heating controlling means to provide electrical feedback to control said wafer heater means;
a wafer insertion and removal means, said wafer insertion and removal means functioning to permit a wafer to be inserted into said chamber for mounting within said wafer holding means, and permitting a wafer to be removed from said wafer holding means and said chamber;
a gas analyzer means, said gas analyzer means being engaged to said chamber and functioning to detect said vaporized volatile contaminants.

13. A surface volatile material detector as described in claim 12 wherein said wafer insertion and removal means includes a sealable gap being formed in said walls of said chamber, said gap being selectively openable to insert or remove a wafer from said chamber, and said gap being closeable such that said chamber walls are sealed.

14. A surface volatile material detector as described in claim 13 wherein said wafer insertion and removal means includes a chamber locking means, said chamber locking means functioning to releasably seal said gap in a closed orientation; said locking means including a guide rail means engaged to the walls of said chamber and functioning to slidably control the opening and closing of said chamber wall gap.

15. A surface volatile material detector as described in claim 12, wherein said heat energy transmissive substance comprises a quartz glass window, said window being disposed within said chamber walls and forming a part thereof, and wherein said wafer heating means comprises an infrared light energy source which is disposed to project infrared energy through said window to illuminate and heat said wafer within said chamber.

16. A surface volatile material detector as described in claim 15, further including a heat energy reflector means, said heat energy reflector means being disposed within said chamber and functioning to reflect heat energy which passes through said wafer back towards said wafer; said heat energy reflector means including a heat reflecting plate, said heat reflecting plate being disposed on a side of said wafer away from said wafer heating means.

17. A surface volatile material detector as described in claim 12 wherein said chamber is filled with a dry, relatively inert gas, and said gas analyzer means comprises a low pressure residual gas analyzer.

18. A method for detecting volatile materials disposed upon the surface of a wafer, comprising:
mounting a wafer within a sealable chamber and sealing said chamber;
heating said wafer to a temperature sufficient to vaporize materials disposed upon the surface thereof utilizing an infrared heating means;
controlling said heating means utilizing an electrical controller;
sensing the temperature of said wafer utilizing a temperature sensing means;
providing an electrical output signal from said temperature sensing means indicative of the temperature of said wafer to said heater controlling means;
controlling the heat energy output of said wafer heating means utilizing said heater controlling means based upon said temperature sensor electrical output signal; and
analyzing the gaseous atmosphere within said chamber utilizing a gas analyzing means subsequent to the heating of said wafer, whereby any vaporized materials present within the atmosphere within said chamber are detected.

19. A method for detecting volatile materials as described in claim 18 further including the steps of:
evacuating said chamber utilizing a vacuum means, whereby a low atmospheric pressure environment is created within said chamber;
introducing a substantially inert gas from a gas source into said chamber to facilitate said detection of said vaporized materials.

20. A method for detecting volatile materials as described in claim 19 further including the steps of:
sampling the atmosphere within said chamber at a known sampling rate to detect said vaporized materials;
bleeding further inert gas from said gas source into said chamber at said known sampling rate to maintain said low atmospheric pressure within said chamber.

* * * * *